United States Patent [19]
Cheeseman

[11] Patent Number: 5,976,886
[45] Date of Patent: Nov. 2, 1999

[54] FLUORESCEIN BLOODSTAIN DETECTION METHOD

[76] Inventor: Robert Cheeseman, 4844 Camino Roberto, Bonita, Calif. 91902

[21] Appl. No.: 08/948,673

[22] Filed: Oct. 9, 1997

Related U.S. Application Data

[60] Provisional application No. 60/028,186, Oct. 15, 1996, abandoned.

[51] Int. Cl.$^6$ .................................................... G01N 21/76
[52] U.S. Cl. ................................ 436/63; 436/66; 436/74; 436/166; 436/172; 356/39
[58] Field of Search ................................. 436/63, 66, 74, 436/134, 172, 166; 356/39; 250/362, 361 C

[56] References Cited

U.S. PATENT DOCUMENTS

| | | | |
|---|---|---|---|
| 4,249,412 | 2/1981 | Townsend, III | 73/40.7 |
| 5,705,470 | 1/1998 | Faris | 510/403 |

OTHER PUBLICATIONS

Maucieri, L.A. et al "Enhancement of Faint and Dilute Bloodstains with Fluorescence Reagents" California Association of Criminalists, 1992.

Thornton, J.I. "Enhancement of the Luminol Test by Means of Light Amplification" Chemical Abstracts, vol. 104, Abstract No. 103690v, 1986.

Everse, K.E. et al "Blood Print Detection by Fluorescence" Chemical Abstracts, vol. 107, Abstract No. 18957e, 1987.

Cheeseman, R., et al. (1995) Fluorescein as a field worthy latent bloodstain detection system. J Forensic Ident. 45 (6):631–646.

*Primary Examiner*—Jeffrey Snay
*Attorney, Agent, or Firm*—Pillsbury, Madison & Sutro, LLP

[57] ABSTRACT

An improved method of detecting latent bloodstains using a thickened solution of fluorescin which is applied to a surface, activated by application of hydrogen peroxide and visualized as fluorescein under ultraviolet (UV) light is disclosed.

14 Claims, 4 Drawing Sheets

FLUORESCEIN BLOODSTAIN DETECTION METHOD

CROSS-REFERENCE TO RELATED APPLICATION

This application claims priority under 35 U.S.C. §119(e) to provisional application No. 60/028,186, filed Oct. 15, 1996.

BACKGROUND OF THE INVENTION

1. Field of the Invention

This invention relates to fluorescent methods of detecting blood, and specifically relates to the use of fluorescein for detection of latent bloodstains on solid surfaces.

2. Relevant Prior Art

In forensic investigations, detection of blood often provides critical information about commission of a crime. Because criminals often attempt to hide evidence of criminal activity, blood is often wiped or washed away from a crime scene. Therefore, detection of latent bloodstains may be the only means of discovering this type of information related to the crime committed.

One method of detecting faint or dilute bloodstains includes spraying the area suspected of containing bloodstains with a chemiluminescent agent (5-amino-2,3-dihydro-1,4-phthalazine, also known as luminol) and then detecting emitted light where the blood is located. Oxidation of luminol is accompanied by a striking emission of light that can be visually or photographically detected. Oxidation of luminol occurs in the presence of iron and peroxides, both of which are generally present in bloodstains. Because of this property, luminol has been one of the most commonly used bloodstain detection reagents. Luminol can also be oxidized by environmentally-present iron, copper, cyanides and peroxides, which can result in high background signals when attempting to locate latent bloodstains in some environments.

In addition, luminol has been characterized as a "possible carcinogenic" on material safety data sheets (MSDS) provided by commercial suppliers to provide consumers with safety information. Because of increased concern by users and regulatory agencies, such as the Environmental Protectional Agency, with respect to toxic and/or mutagenic reagents used in the work place, there is a need for an alternative to luminol for detection of latent bloodstains. Enforcement of more stringent safety guidelines may also have limited the use of luminol. Thus, there is a need for a safe, reliable alternative bloodstain enhancement technique.

Fluorescein (3',6'-dihydroxyspiro[isobenzofuran-1 (3H), 9'-[9H]xanthen]-3-one) and related compounds have been used as fluorescent agents in clinical diagnostics for many years. Fluorescein may be used to detect and locate the position of gastrointestinal bleeding (e.g., see U.S. Pat. No. 3,483,859). U.S. Pat. No. 4,341,223 discloses a fluoresceable composition that includes fluorescein as a tracer for use in the vascular system, particularly for detecting ophthalmic conditions. Fluorescein has been used in angiography diagnostics for vascular ophthalmic disorders (Reichel, E., & Puliafito, C., "Indocyanine Green (ICG) angiography in the diagnosis and treatment of choroidal neovascularization," *Clinical Modules*, New England Eye Center, January 1994). Fluorescein has been combined with other reagents to measure the circulating red cell volume, the total blood volume and red cell survival as disclosed in U.S. Pat. No. 5,536,643. A fluorescein fatty acid monoester has been used diagnostically, where fluorescein released in urine or serum provides a measurement of exocrine pancreatic function as disclosed in U.S. Pat. No. 3,786,140. Fluorescent cell stains have also been used in in vitro diagnostics, such as disclosed in U.S. Pat. No. 4,345,027.

Fluorescein has been widely used in detecting activities associated with biological samples, including blood, and has been suggested as an alternative reagent to replace luminol for detecting bloodstains (Maucieri, L. & Monk, J., "Enhancement of Faint and Dilute Bloodstains With Fluorescence Reagents," Cal. Assoc. Criminalists, Summer 1992). In this process, a fluorescin (2-(3,6-dihydroxy-9H-xanthen-9-yl)-benzoic acid) solution is applied to the bloodstain, and is thereby converted to fluorescein by the peroxide and heme of the blood, to produce a fluorescence. The method may include hydrogen peroxide treatment of the fluorescintreated area to enhance the fluorescence signal. The fluorescein method for detecting latent bloodstains at suspected crime scenes, however, generally has not provided the resolution desired for documentation of evidence when blood has been detected. That is, although the presence of blood may be detected, detail in the pattern of the stain is generally lost due to running and smearing of the stain during processing, particularly if the stain is on a relatively non-porous and vertical surface. Hence, there is a need for a method of detecting latent bloodstains that does not require the use of luminol, that provides sensitivity for detecting small amounts of blood on a variety of surfaces, and that provides sufficient resolution to detect pattern characteristics and details of latent bloodstains.

In addition, production of the fluorescin solution used in the fluorescein detection method involves relatively complex chemical procedures (i.e., a refluxing reaction) that can only be performed by those with sufficient training and equipment. Because a relatively fresh fluorescin solution is required to practice a fluorescein detection method, this limits use of the method to those facilities that have the capacity to perform the chemical steps needed to produce the reagent. Thus, there is also a need for a relatively simple method of producing fluorescin reagent.

SUMMARY OF THE INVENTION

The present invention includes methods for detecting latent bloodstains by applying a thickened fluorescin solution, a dilute hydrogen peroxide solution, which may also contain a thickening agent, to enhance conversion of fluorescin to fluorescein, and illuminating the area with an alternate light source of about 435 nm to about 505 nm to detect the presence of fluorescein. Because the thickened solution or solutions can be applied to a variety of surfaces (e.g., vertical walls or carpeting with an uneven texture) without significant spreading or running of the applied reagents, this fluorescein detection method does not distort the bloodstain pattern on the surface. Thus, this method provides sufficient detail to detect patterns (e.g., shoe prints or spatter patterns) often associated with bloodstains at a crime scene. Also included in the invention is a kit of reagents suitable for using the fluorescein detection method at a suspected or known crime scene.

According to the invention, there is provided a method for detecting latent blood on a solid surface, that includes the steps of providing a surface suspected of containing a latent bloodstain, spraying the surface with a fluorescin reagent solution that includes about 0.006% to about 0.33% fluorescin, 0.06% to about 3.33% sodium hydroxide and an alkaline-insensitive thickening agent in an aqueous solution, then spraying the surface with an about 2% to about 15% hydrogen peroxide solution, and detecting fluorescence emitted from fluorescein that results from conversion of fluorescin to fluorescein due to the presence of latent blood contained on the surface. In one embodiment, the spraying step with a fluorescin reagent solution is repeated before the spraying step with a hydrogen peroxide solution. The spraying step with a fluorescin reagent solution is preferably performed using a pressurized spray device, whereas the spraying step with a hydrogen peroxide solution is performed using a hand pump spray device. In one embodiment, the detecting step includes illuminating the surface with an alternate light source of about 435 nm to about 505 nm, and preferably by illuminating with a 450 nm light source and photographically documenting the fluorescence emitted. In one embodiment, the fluorescein reagent solution is prepared from about a 1:3 to about 1:150 dilution of a first solution of about 1% fluorescin and 10% sodium hydroxide, in a second aqueous solution containing an alkaline-insensitive water soluble gum. Preferably, the second aqueous solution contains about 1% to about 10% of an alkaline-insensitive water soluble gum, and more preferrably about 0.5% Xanthan gum. In another preferred embodiment, the hydrogen peroxide solution is about 3% to about 10% hydrogen peroxide. The detecting step is capable of detecting blood diluted about 1:6,000 to about 1:105,000, preferably is capable of detecting blood diluted about 1:6,000 to about 1:75,000, and more preferably is capable of detecting blood diluted about 1:6,000 to about 1:15,000. In one embodiment of the method, the detecting step is capable of detecting latent blood on a nonporous, vertical or uneven surface and retaining a pattern of the latent blood for sufficient time to allow documentation of the fluorescence emitted. The invention also includes a blood specimen treated according to this method.

According to another aspect of the invention, there is provided a method of producing an aqueous fluorescin solution, that includes the steps of mixing fluorescein into a 10% sodium hydroxide aqueous solution to produce a fluorescein and sodium hydroxide mixture, adding zinc particles to the fluorescein and sodium hydroxide mixture, heating the fluorescein and sodium hydroxide mixture to which zinc particles have been added to boiling until the fluorescein and sodium hydroxide mixture produces a colorless solution containing powdered zinc, allowing the colorless solution containing zinc particles to cool, and separating the colorless solution from the zinc particles. In one embodiment, the mixing step includes mixing about 1% by weight of fluorescein in about 99% by weight of a 10% sodium hydroxide aqueous solution, the adding step includes adding about 10% by weight of 20 mesh zinc particles, the heating step includes heating the fluorescein and sodium hydroxide mixture to which zinc particles have been added to about boiling in a non-refluxing containing, and the separating step includes decanting the colorless solution away from the zinc particles. Another embodiment is a fluorescin solution produced by this method.

According to another aspect of the invention, there is provided a method of producing an aqueous fluorescin solution, in which about 1 g of fluorescein is mixed with about 100 ml of a 10% sodium hydroxide aqueous solution and heated in the presence of about 10 g of zinc to produce a colorless fluorescin solution, wherein the improvement of the method includes heating the mixture of fluorescein and 10% sodium hydroxide aqueous solution with about 20 mesh zinc particles to about boiling in a non-refluxing container to produce a nearly colorless fluorescin solution containing zinc particles, and decanting the colorless fluorescin solution from the zinc particles.

According to another aspect of the invention, there is provided a kit for providing reagents used in detecting latent bloodstains. The kit includes sodium hydroxide, zinc particles, fluorescein, an aqueous solution of an alkaline-insensitive thickening agent, and a hydrogen peroxide solution, wherein all dry compounds (e.g., sodium hydroxide, zinc particles and fluorescein) contained in the kit are provided in premeasured aliquots. Preferably, the kit includes a 10% aqueous NaOH solution or pre-measured pellets, stored in a non-reactive container, 20 mesh zinc particles, a premeasured aliquot of fluorescein, an aqueous solution of Xanthan gum at about 0.25% to about 0.5%, and a 3% to 10% hydrogen peroxide solution. The kit may also include any glassware or hardware needed to practice the method such as flasks and an alternate light source.

It should be understood that both the foregoing general description and the following detailed description are exemplary only and are not restrictive of the invention as claimed. The accompanying figures, which are incorporated in and constitute a part of the specification, illustrate various embodiments of the invention and, together with the description, serve to explain the principles of the invention.

DETAILED DESCRIPTION OF THE INVENTION

Figure 1:
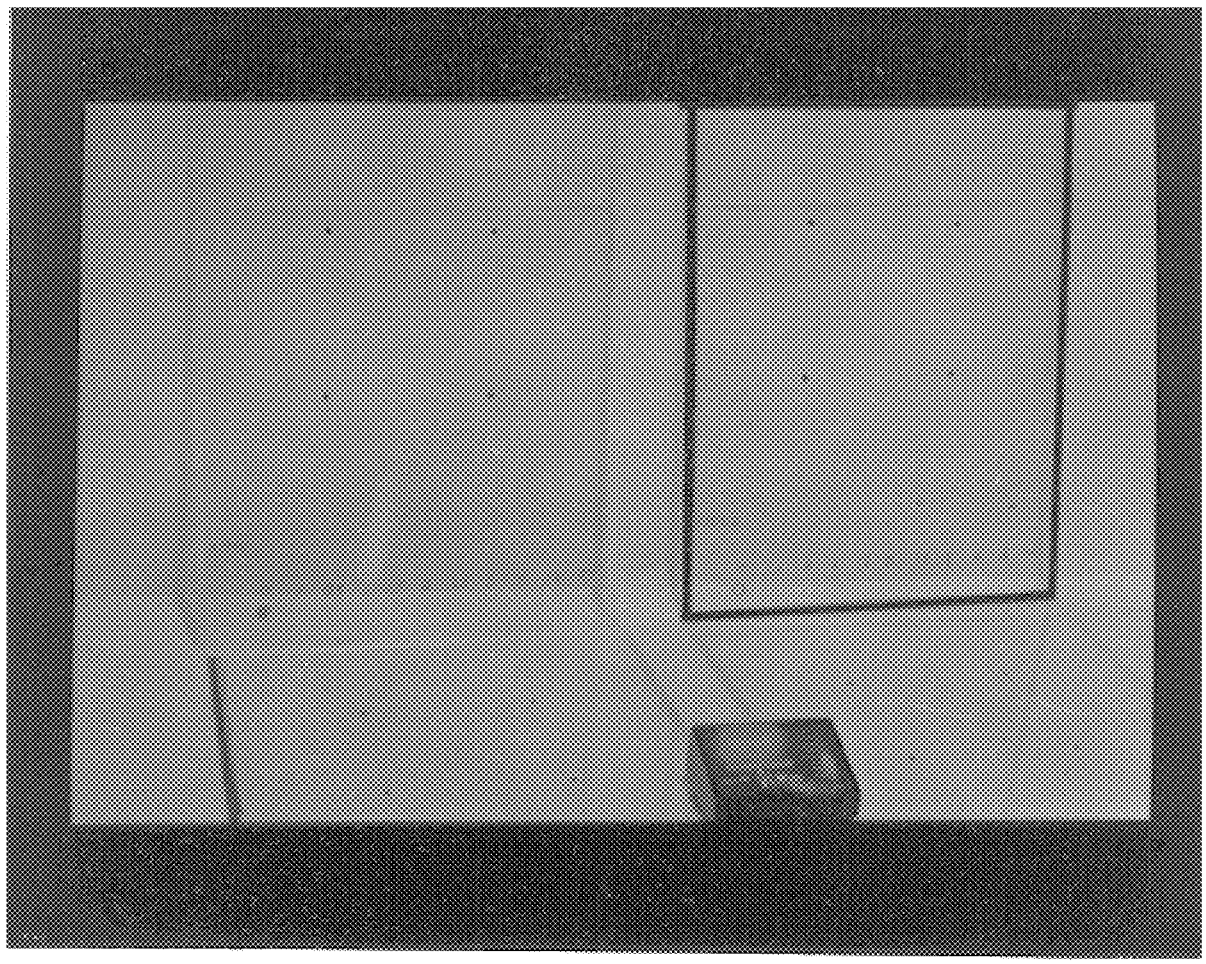
FIG. 1 is a photograph taken under natural light using a barrier filter (orange) showing two vertically-positioned and two horizontally-positioned glass panes to which blood was applied in a punctate pattern (spots in a 10×10 grid) and allowed to dry.

The fluorescein detection method is useful for detecting latent bloodstains on solid surfaces. This method depends on the conversion of fluorescin, a relatively colorless reagent, to fluorescein, the fluorescent compound detected when illuminated with UV light. Oxidation by blood chemicals (e.g., peroxidases or heme components) of fluorescin produces fluorescein. The conversion of fluorescin to fluorescein is enhanced by the application of hydrogen peroxide (about 1% to 10%) to the fluorescin reagent after it is applied to the bloodstain. The present fluorescein detection method includes thickening agents in at least the fluorescin reagent to limit distortion of the detected bloodstain, and optimizes the concentrations of reagents for convenient detection of very dilute blood samples. The method also uses a simplified method of producing the fluorescin reagent, suitable for use with a minimum of equipment and by personnel with minimal training in chemical procedures.

Two factors that generally bear on the effective use of this technique are the surface on which the bloodstain is located and the blood concentration in the stain. In some situations, the blood concentration may have become so diluted (e.g., due to washing or environmental factors) that detection is limited. If neat bloodstains are found, adequate samples may be taken for serological testing before the fluorescein detection method is employed. Because one reagent used in the fluorescein detection method is alkaline, other humoral analyses (e.g., ABO blood typing, secretor status or use of anti-human antibodies) may not be possible after the technique has been used. However, DNA analysis using polymerase chain reaction (PCR) amplification procedures has been successfully used after the fluorescein detection method was used on a bloodstain. Therefore, the fluorescein detection method may be used to first locate a latent bloodstain and other techniques such as PCR amplification then may be used on samples taken from the detected bloodstain.

Fluorescence resulting from latent bloodstains is more readily detected on dark colored surfaces than on light backgrounds (e.g., yellow materials) because the contrast differential is enhanced by the darker background. The substrate surface texture upon which the bloodstain is located also may affect the detection results. Generally, performance of blood detection methods that use fluid reagents is affected by the porosity and orientation of the surface to which the reagents are applied. Porous substrates are more difficult to completely clean, hence, it is less probably the stain will be totally removed; however, the greatest sensitivity is achieved on nonporous substrates due to the fact that the bloodstain cannot penetrate the substrate and is therefore easier to remove by cleaing. As a result, bloodstains are generally more readily detected on porous surfaces compared to non-porous surfaces, and stains on vertical surfaces are generally more distorted due to running or smearing of the reagents compared to that of horizontal surfaces. Uneven or curvilinear surfaces are also prone to smearing or uneven diffusion of the fluid reagents, thus distorting the image of the bloodstain detected by fluorescence. To alleviate problems associated with detecting bloodstains on non-porous, vertical or uneven surfaces, the present method includes a thickening agent to keep the reagents in place on the sample without significant running or spreading for sufficient time to detect and record the fluorescence associated with the treated stain. Use of a thickening agent in the fluorescein method reagents helped to slow the dispersion or distortion of the bloodstain pattern after the reagents were applied, thus preserving the bloodstain pattern for documentation and pattern analysis.

The method involves the following procedures. First, a thickened fluorescin reagent is sprayed onto the surface of interest where a latent bloodstain may be present. Optimally, two applications of a nebulized thickened fluorescin reagent is applied to evenly coat the surface. The fluorescin reagent is preferably freshly prepared before use, preferably using a simplified gentle boiling method described herein. Immediately following the last application of the fluorescin reagent, a dilute hydrogen peroxide solution is applied to the surface coated with the fluorescin reagent. The hydrogen peroxide solution is a dilute solution that is also preferably applied by spraying a nebulized solution on the coated surface. Then, the surface is illuminated with an alternate light source, preferably producing light of about 435 nm to about 505 nm (e.g., a long wave UV source), more preferably a 450 nm light source. Where the fluorescin reagent has been oxidized to fluorescein, fluorescence is emitted which can readily be recorded with standard photographic methods (still frame or video photography). The contrast between background emission and sample-dependent fluorescence can be optimized by appropriately filtering the light using a yellow or orange filter attached to the photographic equipment. Because the method is relatively rapid and uses at least one reagent that remains substantially adhered to the surface being tested, the detected fluorescence resulting from a latent bloodstain maintains the shape and pattern of the bloodstain being detected. This enhanced preservation of the shape of the detected bloodstain is particularly advantageous for preserving a bloodstain pattern for documentation and use as forensic evidence.

In its reduced (colorless) state, fluorescin has a relatively short shelf life, and it is preferably used within about 24 to 48 hr after preparation to avoid background fluorescence caused by oxidation of the reagent (Monk, J. W., "Fluorescent Bloodstain Detection—A Replacement for Luminol", MSc project report to CCI, 1991; Maucieri, L. & Monk, J., "Enhancement of Faint and Dilute Bloodstains With Fluorescence Reagents," Cal. Assoc. Criminalists, Summer 1992). Because freshly prepared fluorescein reagent is preferred, field preparation of the reagents using premeasured components provided in a kit was adopted. This kit format and the simplified gentle boiling preparation procedure disclosed herein allows those skilled in the art (e.g., crime scene technicians) to readily use the method in the field. Minimizing the equipment and skill required to prepare the fluorescein reagent is critical to its success in the field.

The reagents are applied to a surface suspected of having a latent bloodstain as a spray of small droplets (i.e., as a nebulized solution), such as are produced using any standard hand-held pump sprayer or other device for producing an aerosol. Suitable sprayers include a non-refluxing type aerosol sprayer, an airless (i.e., propellant-based) sprayer, jet nebulizers, ultrasonic nebulizers, metered dose atomizers and the like. An air gun sprayer or airless gun sprayer is useful for producing uniform droplet sizes. Non-refluxing nebulizers, in which the nebulization energy is supplied by electrical vibration or mechanical pressure rather than dynamic air flow, may be used to minimize evaporation and produce relatively uniform sized droplets. A propellant aerosol nebulizer is a self-contained closed system that delivers a continuous spray or dispenses metered amounts. Conventional closed propellant aerosol nebulizers or conventional air sprayers (analogous to those commonly used in paint spraying) may be used, in which the reagent is contained in a container attached to a nozzle through which pressurized air is projected, thus creating the aerosol. The container itself may be sealed or contain an inert gas to protect the reagent composition from exposure to air before use. An inert gas may be used in place of pressurized air as the propellant to further minimize exposure to air. Airless sprayers are similar to air sprayers but eliminate the relatively large volume of air that is normally used to nebulize the fluid. Conventional airless sprayers, such as those used to minimize overspray in painting, may be miniaturized for use in nebulizing the reagent compositions for use in field operations. Continuous spray nozzles are generally used with air or airless sprayers and the amount applied is controlled by the length of time the spray is administered. The construction of the nozzles for any of these spray devices uses conventional technology to produce micrometer sized droplets.

Because of the viscosity of the thickened reagents, a power sprayer is preferred for those reagents to produce even and consistent coverage for the target area. Unthickened reagents (e.g., dilute hydrogen peroxide) may be conveniently dispensed using a conventional hand-held spray pump bottle. For the thickened fluorescin reagent solution, a pressurized spray device is preferred because of its capacity spray the higher viscosity solution and deliver the reagent in a controlled, contained and detailed manner.

The following materials and methods have been used in practicing this fluorescein detection method: fluorescein ($C_{20}H_{10}O_5Na_2$, FW=376.28), NaOH, zinc (20 mesh, Fisher Scientific Co., Tustin, Calif.), Xanthan gum (KELTROL RD™), hydrogen peroxide ($H_2O_2$), a conventional hot plate with a stirrer, standard laboratory glassware, conventional hand-held pump spray bottles and a LPHV power spray gun (such as are available from commercial hardware stores). For visualizing and documenting the fluorescence the following equipment was used: an alternate light source (about 435 to 505 nm, preferably 450 nm), a standard 35 mm SLR camera or video camera, preferably with an orange or yellow barrier filter (e.g., available from Nikon) and, as needed, a tripod for the camera. A Wood lamp, an argon laser (Omni-1000) light source and other alternate light sources have been successfully used. For personal safety, a particle face mask, UV-protective eye goggles or glasses, latex gloves and clothing cover (e.g., a laboratory coat or smock) should be used in conventional ways well known to those skilled in the art.

The aqueous solution containing a thickening agent may be prepared using any conventional thickening agent that retains viscosity when an alkaline solution is added to it. Optimally, a thickening agent will meet three criteria: 1) it must be able to tolerate the high pH of the fluorescin solution without detrimental effects to its thickening properties; 2) it must not cross-react with the fluorescin, or cause any detrimental effects on the fluorescin's properties (cross-reactivity would be known immediately when the thickened solution is tested on a negative and positive control); and 3) it must be capable of being applied in an even and consistent manner but be viscous enough to prevent reagent running and, thus, establish bloodstain pattern stabilization long enough for documentation. For example, a variety of gums or polymers purified from natural sources or synthetic polymers are suitable, such as, purified Xanthan gum, guar gum, gelatin (glycine), Ghatti gum, acacia gum and others well known in the art (cf. C. L. Mantell, *The Water-Soluble Gums*, New York, 1947; F. Smith & R. Montgomery, *The Chemistry of Plant Gums and Mucilages*, Reinhold, New York, 1959; and *Industrial Gums*, 2nd ed., R. L. Whistler, Ed., Academic Press, New York, 1973), or polyethylene glycol (PEG) may be used. To achieve adequate viscosity for spray application of the resulting dilutions, a 1% to 25% aqueous solution of the thickening agent may be used, with the viscosity being determined by the polymer size such as is well known to those skilled in the art. A viscosity that substantially prevents spreading or running on a vertical non-porous surface, when the aqueous solution has been used as a fluorescin/sodium hydroxide diluent as described above, during a time period of about 30 sec to 5 min, is suitable for use in preparing the reagents used in this method.

A preferred thickening agent is xanthan gum, an exocellular heteropolysaccharide produced via fermentation (e.g., KELTROL RD™, described in *Xanthan Gum Booklet*, "Xanthan Gum—Natural Biogum for Scientific Water Control", Fifth Ed., Kelco Company, San Diego, Calif., June 1986; *Technical Bulletin* DB-31, "Preservatives for Kelco Polymers Used in Industrial Applications", Kelco Company, San Diego, Calif., November 1986; *Technical Bulletin* DB-38, and "KELTROL RD™ Xanthan Gum in Food, Personal Care and Pharmaceuticals," Kelco Company, San Diego, Calif., June 1994). This thickener was preferred because it dissolves readily in aqueous solutions and is relatively inexpensive. Other thickeners with the same viscosity characteristics that are not affected by alkaline solutions are equally useful in the reagents used in the present method.

A Xanthan gum solution of about 0.25% to about 0.5% was used as the thickener. A preferred 0.5% Xanthan gum solution was prepared by mixing approximately 5.0 grams of purified Xanthan gum in 1 liter of deionized water. Preferably, the Xanthan gum thickener is a purified fermentation product (e.g., KELTROL RD™). Because the Xanthan gum thickener dissolves relatively slowly, it is preferably dissolved in advance of making the dilution with the fluorescein/sodium hydroxide solution. To facilitate dissolving the Xanthan gum, the water may be heated to about 50° C. to about 90° C. during solution preparation. The aqueous Xanthan gum solution may be stored frozen (e.g., at −20° C.) and thawed before use in the dilution.

For use, about 300 ml of the fluorescin reagent solution is placed in a first spray container. When the fluorescin reagent solution is thickened with Xanthan gum, the spray container is preferably one that provides positive pressure to dispense the solution.

Preparation of the Hydrogen Peroxide Solution. A 10% hydrogen peroxide solution was prepared by mixing 1 part of a 30% hydrogen peroxide solution with 2 parts of deionized water. For example, 100 ml of 30% $H_2O_2$ was mixed with 200 ml of deionized water. This hydrogen peroxide stock solution may be stored refrigerated (e.g., 5° C.) in an opaque bottle. Alternatively, for convenience, a prepared commercially available 3% hydrogen peroxide solution, such as generally is available from a pharmacy, may be used as the stock solution. It will be appreciated that the hydrogen peroxide solution may vary from about 2% to about 15% and still be effective in the present method. For use, about 300 ml of the 3% or 10% stock solution was placed in a standard hand-held pump spray bottle.

The method of applying the reagents to visualize latent bloodstains includes the step of spraying a 1:20 to 1:50 fluorescin reagent solution on the area of interest by applying a fine mist of uniform density from a distance of about 30 cm to about 46 cm (about 12 to 18 in). Preferably, two applications of the fluorescin reagent solution are made in this fashion, taking care not to make the misting so heavy as to cause the reagent to run. Two separate spray applications are preferred for this technique, using a light and even misting to provide the most successful results. The fluorescin reagent solution is allowed to contact the area of interest from about 5 sec to about 60 sec to allow the fluorescent color to develop where the fluorescin reagent solution contacts blood. The next step is spraying the hydrogen peroxide dilution solution onto the fluorescein-treated area, applying a mist in substantially the manner described above except that a hand-held pump sprayer may be readily used if the hydrogen peroxide solution does not contain a thickening agent. After the user has properly attached UV safety glasses or goggles, the area of interest is illuminated with near UV light (450 nm) to allow the fluorescein to fluoresce.

Application of the fluorescin reagent solution to the targeted area of bloodstain results in a yellow colorization in the area where blood is detected within a few seconds. At this stage, the bloodstain may be apparent and some background colorization also may be apparent. The application of the dilute hydrogen peroxide solution helps digest the heme-compounds in blood, exposing more peroxidase activity to react with the fluorescin. Thus it enhances and clarifies the bloodstain pattern because the fluorescence becomes more intense and the stain pattern stands out more from the background. Using a near UV light source, the bloodstained areas fluoresce when illuminated.

As controls, a strongly reactive control, a weakly reactive control and a negative control may be performed immediately before routine examination of an area suspected of having latent bloodstains. Preferably, the substrate of the area of interest should be simulated or an actual portion of the area of interest, properly labeled, should be utilized. Such controls are particularly important if the substrate is one that can produce false positive results (e.g., iron or copper containing or contaminated surfaces or bacterial contamination such as from soil bacteria).

This method enhances the appearance of latent bloodstain patterns. While it cannot differentiate the blood type, or source of the bloodstain or its age, it can provide information on the bloodstain and activities associated with the bloodstain. For example, the spattering or spreading pattern of a bloodstain may be used to determine the position of the source relative to the surface on which the bloodstain is detected. Thus, the pattern of blood may indicate whether the stain resulted from an entry wound, for example, such as caused by a knife, or whether it resulted from pooling blood following a wound received at another location. Moreover, articles of clothing such as shoes or jackets may retain patterns of bloodstains indicating that the article of clothing was worn at the scene of a crime in which blood was present. Visualizing a totally latent foot trail created by a bloodstained shoe may lead the investigator to additional prints on a more favorable substrate or provide information to identify individual characteristics of a shoe present at the scene of a crime or other evidence. The method has been used to detect blood on an article that had been stored in custody for about 17 years.

Because this technique may be one of the last procedures performed at a crime scene, it is possible for the crime scene investigators to notify the laboratory to prepare the fluorescin reagent and transport it to the crime scene just before it is needed. Alternatively, the fluorescin reagent may be prepared at a crime site if the necessary equipment is brought with investigators and an electrical source is available for boiling the reagent as described herein. Protection of the fluorescin reagent in darkened opaque nonreactive bottles is necessary to prevent exposure of the reduced (colorless state) fluorescin to sunlight or any UV light source may prematurely oxidize the fluorescin back to the oxidized fluorescein (colored state), hence undermining the effectiveness of the method.

This technique is optimally applied once to a target area. Each time a bloodstain is sprayed, to some degree dispersion of the pattern (distortion) is expected to occur. Also, the background fluorescence increases on target areas which have been previously treated.

The present method simplifies the chemical procedures used for reducing fluorescein to fluorescin. It also provides increased sensitivity and specificity of detection by using optimum working dilutions. It resolves the problems associated with the reagent running or spreading, hence expanding opportunity to document and analyze detected bloodstains using standard photographic procedures.

The invention can be better understood by way of the following examples which are representative of the preferred embodiments, but which are not to be construed as limiting the scope of the invention.

EXAMPLE 1

Simplification Procedure for Making the Fluorescin Reagent Solution

In the prior art, fluorescein (the fluorescent compound in an oxidized color state) was reduced to fluorescin (the fluorescent compound in its reduced colorless state) by heating the fluorescein (1.0 g) in 10% NaOH (100 ml) containing zinc powder (10 g) using a refluxing column to prevent evaporation of the solution. Such a procedure requires specialized equipment and some training in chemical procedures, making it inconvenient or impossible for use in non-laboratory (e.g. field) settings.

The present procedure eliminates of the refluxing apparatus by bringing the solution to a gentle boil or near boiling which provides an effective fluorescin solution. This method can be readily used by personnel with a minimum of equipment and training, and can be used outside of a laboratory particularly if premeasured reagents are provided.

A fluorescein/sodium hydroxide solution was prepared by dissolving 1.0 g of fluorescein in 100 ml of a 10% sodium hydroxide stock solution. The 10% sodium hydroxide stock solution was prepared by dissolving 10.0 g of sodium hydroxide in 100 ml of deionized water. This sodium hydroxide stock solution may be stored in a nonreactive nonglass container (e.g., polypropylene bottle such as available from Nalgene). The fluorescein and sodium hydroxide stock solution were mixed in standard laboratory glassware (e.g., 250 ml Erlenmeyer flask) using an automatic stirring device to facilitate dissolving.

The flask containing the 1% fluorescein and 10% sodium hydroxide solution was placed on a hot plate with a stirring device and the solution was stirred and heated gently (to about 30° C. to about 50° C.). Then, 10.0 g of zinc pellets were added to the solution which was further heated and stirred until it was near boiling or gently boiling. During this process, the zinc does not dissolve but the solution loses most of its color, becoming nearly clear and colorless except for the color of the zinc particles (i.e., becoming a 1% fluorescin/10% sodium hydroxide solution with suspended zinc particles). After the solution had reached about the boiling point or boiled gently, the solution was allowed to cool at room temperature, during which time the zinc particles settled to the bottom of the container.

The cooled fluorescin solution was decanted carefully into a clean second container, leaving the undissolved zinc in the first container. This decanted 1% fluorescin/10% sodium hydroxide solution was then diluted in a range of about 1:20 to about 1:50 with deionized water containing about 0.5% dissolved thickening agent (preparation of the thickening agent solution is described herein below). Thus, the resulting fluorescin reagent is about a 0.02% fluorescin/0.2% NaOH solution to about a 0.05% fluorescin/0.5% NaOH solution.

A 1:20 dilution was prepared by mixing 1 part of the decanted solution with 19 parts of deionized water containing 0.5% dissolved Xanthan gum. For example, a 1:20 dilution was made by mixing thoroughly 50 ml of the decanted solution with 950 ml of deionized water containing 0.5% dissolved Xanthan gum (KELTROL RD™, Kelco Co., San Diego, Calif.). Similarly, a 1:40 dilution was made by mixing thoroughly 25 ml of the decanted solution with 975 ml of the 0.5% Xanthan gum aqueous solution; and a 1:50 dilution was made by mixing thoroughly 20 ml of the decanted solution with 980 ml of the 0.5% Xanthan gum aqueous solution. The resulting dilutions are referred to as the "fluorescin reagent solution" with the appropriate dilution indicated as a prefix (e.g., a 1:50 fluorescin reagent solution).

EXAMPLE 2

Comparison of Sensitivity of Fluorescin Reagent Prepared by Simplified Method and Refluxing Method To determine if any sensitivity was lost due to use of the simplified procedure, the following experiment was conducted. The fluorescin reagent was prepared by either the simplified boiling method described in Example 1 or the prior art refluxing method essentially as described earlier (Monk, J. W., "Fluorescent Bloodstain Detection—A Replacement for Luminol", MSc project report to CCI, 1991; Maucieri, L. & Monk, J., "Enhancement of Faint and Dilute Bloodstains With Fluorescence Reagents," Cal. Assoc. Criminalists, Summer 1992).

Utilizing human blood at a range of dilutions in deionized water, ranging from 1:1,000 to 1:105,000, two racks of test tubes (12×75 mm) were set up. Each tube received equal portions (about 30 μl) of: the blood dilution, the fluorescin reagent without a thickening agent (diluted 1:3 in water) and a 10% $H_2O_2$ solution. The tubes in Rack A received fluorescin reagent prepared by the refluxing method, and tubes in Rack B received fluorescin reagent prepared by the simplified boiling method described in Example 1. Negative controls (blanks) were used with each rack in which deionized water was substituted for the blood dilution. After thoroughly mixing all of the components in the tubes, both racks were illuminated with a long wave UV source (Wood's lamp). Fluorescence results for each tube was visually detected and the results were graded and recorded using a plus or minus system, where a plus indicated detectable fluorescence and a minus indicated no detectable fluorescence. Equal results were achieved with each blood dilution and blank, establishing that the sensitivity was positive at a blood dilution of up to 1:105,000. Thus, the simplified boiling method for producing the fluorescin reagent works as well as the more complex refluxing method.

EXAMPLE 2

Specificity of the Detection Method

This example shows that only a few common substances produce fluorescence when a surface stained with the substance is treated using the fluorescein detection method, thus producing false positive results. All of the tested items are typically found in residential settings and may be mistaken for blood by either coloration of an untreated stain (red to brown in color), or reaction with the fluorescin reagent (i.e., fluorescence following use of the fluorescein detection method).

Table 1 shows that many of the substances applied to a solid surface (i.e., poster board) gave some fluorescence when illuminated with 450 nm light ("Inherent"), but most did not react under the conditions of the fluorescein detection method ("Test"). Positive (+) or marginally positive (±) reactions were only observed with five substances, which are probably due to the presence of peroxidases (beet juice, horseradish and urine), metal oxidation (rusted steel and copper) or possibly occult blood (urine). The control bloodstain was positive as expected when tested with the fluorescein detection method but did not have any detectable inherent fluorescence. Based on these results, the fluorescein detection method will generally not produce false positives when used with common substances that may appear to be latent bloodstains.

TABLE 1

| Stained Items | Fluorescence Inherent | Test |
|---|---|---|
| Control blood | − | + |
| Saliva | − | − |
| Coffee | + | − |
| Tea | − | − |
| Grass stains | − | − |
| Soil* | − | − |
| Chocolate | ± | − |
| Cola | + | − |
| Strawberry jelly | + | − |
| Ketchup | ± | − |
| Beet juice | + | ± |
| Horseradish | + | + |
| Cherry-strawberry juice | ± | − |
| Cherry-cranberry juice | ± | − |
| Urine | − | ± |
| Steel | − | − |
| Steel (with rust) | − | ± |
| Aluminum | − | − |
| Copper | − | + |

*Soils may vary greatly from one location to another and the amount and type of living matter contained therein.

EXAMPLE 3

Effective Dilutions for Detection of Blood

The optimum fluorescin dilutions to use for detection of different amounts of blood were determined in two separate tests of the fluorescein detection method. In the first experiment, performed in test tubes substantially as described in Example 2, varying dilutions of fluorescin ranging from 1:3 to 1:150 were tested against blood dilutions ranging from 1:6,000 to 1:105,000. The results of this test are shown in Table 2, in which fluorescence was graded on a 0 to 4 scale, where 0 means no fluorescence was detected and "4" means the most fluorescence was detected, with proportionate amounts therebetween indicated by 0.5, 1, 2 and 3. The least detectable amount of fluorescence was graded 0.5, and "1" indicates clearly detectable fluorescence.

As can be seen from the results in Table 2, using the fluorescin reagent prepared by the simplified boiling method described in Example 1, blood diluted 1:75,000 was clearly detectable with a dilution up to 1:50 of the fluorescin reagent (i.e., with a 1:50 fluorescein reagent solution). At greater dilutions of the fluorescin reagent (1:100 and 1:150) blood was still detectable when the blood was less dilute (1:36,000 or 1:12,000, respectively). As will be understood by those skilled in the art, less dilute blood (e.g., 1:6,000 or 1:12,000) was more readily detectable than more dilute blood, resulting in greater amounts of fluorescence when more fluorescin was present (e.g., at 1:50 dilution compared to the 1:150 dilution). Based on these results, the sensitivity of the 1:50 fluorescin reagent solution seems to be optimal for most blood concentrations.

TABLE 2

| Blood Dilutions × 1000: | | | | | | | | | | Fluorescin Dilutions |
|---|---|---|---|---|---|---|---|---|---|---|
| 6 | 12 | 15 | 24 | 36 | 48 | 75 | 96 | 105 | Blank | |
| 4 | 4 | 3 | 3 | 2 | 1 | 1 | 0.5 | 0.5 | 0 | 1:3 |
| 4 | 3 | 3 | 2 | 2 | 1 | 1 | 0.5 | 0.5 | 0 | 1:50 |
| 2 | 2 | 1 | 1 | 1 | 0.5 | 0.5 | 0 | 0 | 0 | 1:100 |
| 1 | 1 | 0.5 | 0 | 0 | 0 | 0 | 0 | 0 | 0 | 1:150 |

In a second experiment, varying blood dilutions were absorbed into strips of blotter paper and tested using fluorescin dilutions ranging from 1:3 to 1:50. Due to the different substrate, the blood dilutions tested were changed to 1:1,000 to 1:24,000. The fluorescein test method in this experiment was performed using a fluorescin reagent that did not include thickener, which was sprayed as a mist onto the surface using a standard hand-held pump type sprayer. Thickener was not needed because of the absorbent nature of the blotter paper. The results, presented as a simple plus/minus grading system substantially as described in Example 2, are listed in Table 3.

As can be seen from the results shown in Table 3, blood diluted to as much as 1:24,000 was detectable with a 1:3 fluorescin dilution, and at greater fluorescin dilutions, less-diluted blood samples were also detectable (e.g., a 1:50 fluorescin reagent solution detected blood at 1:3,000 dilution). Based of the results presented in Table 2 and 3, it is clear that varying dilutions of the fluorescin reagent solution may be effectively used to detect relatively small amounts of blood.

TABLE 3

| Blood Dilution Factors: | | | | | | | | |
|---|---|---|---|---|---|---|---|---|
| 1000 | 1500 | 2000 | 2500 | 3000 | 6000 | 12000 | 24000 | Fluorescin Dilutions |
| + | + | + | + | + | + | + | ± | 1:3 |
| + | + | + | + | + | + | ± | − | 1:10 |
| + | + | + | + | + | ± | − | − | 1:20 |
| + | + | + | + | + | ± | − | − | 1:30 |
| + | + | + | + | + | ± | − | − | 1:40 |
| + | + | + | + | ± | − | − | − | 1:50 |

EXAMPLE 4
Improved Resolution of Bloodstains Using Thickened Reagents

Smearing or running of fluid reagents has been cited as a significant shortcoming of other blood detection methods (Monk, J. W., "Fluorescent Bloodstain Detection—A Replacement for Luminol", MSc project report to CCI, 1991). Preventing smearing or running improves documentation of detection of bloodstains, particularly in the field for later use of the information in court proceedings. Therefore, a commercially available thickening agent was used to increase the viscosity of reagents used in this fluorescein detection method. In this example, Xanthan gum (KELTROL RD™, Kelco Company, San Diego, Calif.) was used to thicken the fluorescin solution. A blood sensitivity gradient test was conducted (substantially as described in Example 2) without any negative side effect. A variety of dilutions of thickener were tested to optimize the viscosity and delivery system used. As expected, the more viscous the solution, the harder it was to deliver it in a spray using a hand pump spray bottle. For KELTROL RD™ solutions of ≦0.2% per volume, a hand pump spray bottle was effective for delivery but the viscosity was not sufficient to prevent running of the solution. It was apparent immediately that a hand pump delivery system would not deliver the thickened reagent well enough to alleviate the reagent running problem. For KELTROL RD™ solutions of 0.3% to 0.6% per volume, a power spray device was optimal.

For this example, four standard glass panes were stained with blood in a 10×10 grid pattern by applying an aqueous blood solution (1:300 dilution) to the glass using a cotton applicator and a stencil to provide the grid pattern. The blood was allowed to dry. The amount of blood applied was barely detectable on the glass panes under regular light (see FIG. 1). The four panes were then arranged in two sets of two panes each, with each set having one vertical pane and one horizontal pane. All horizontal and vertical glass panes were similarly bloodstained. The fluorescein detection method was then used to visualize the stains, by spraying a thickened 1:50 fluorescin reagent solution on the panes in two separate applications using a power spray delivery device. A 1.0% stock solution of KELTROL RD™ was diluted to the desired viscosity (0.5%) and used as the fluorescin diluent.

Figure 2:
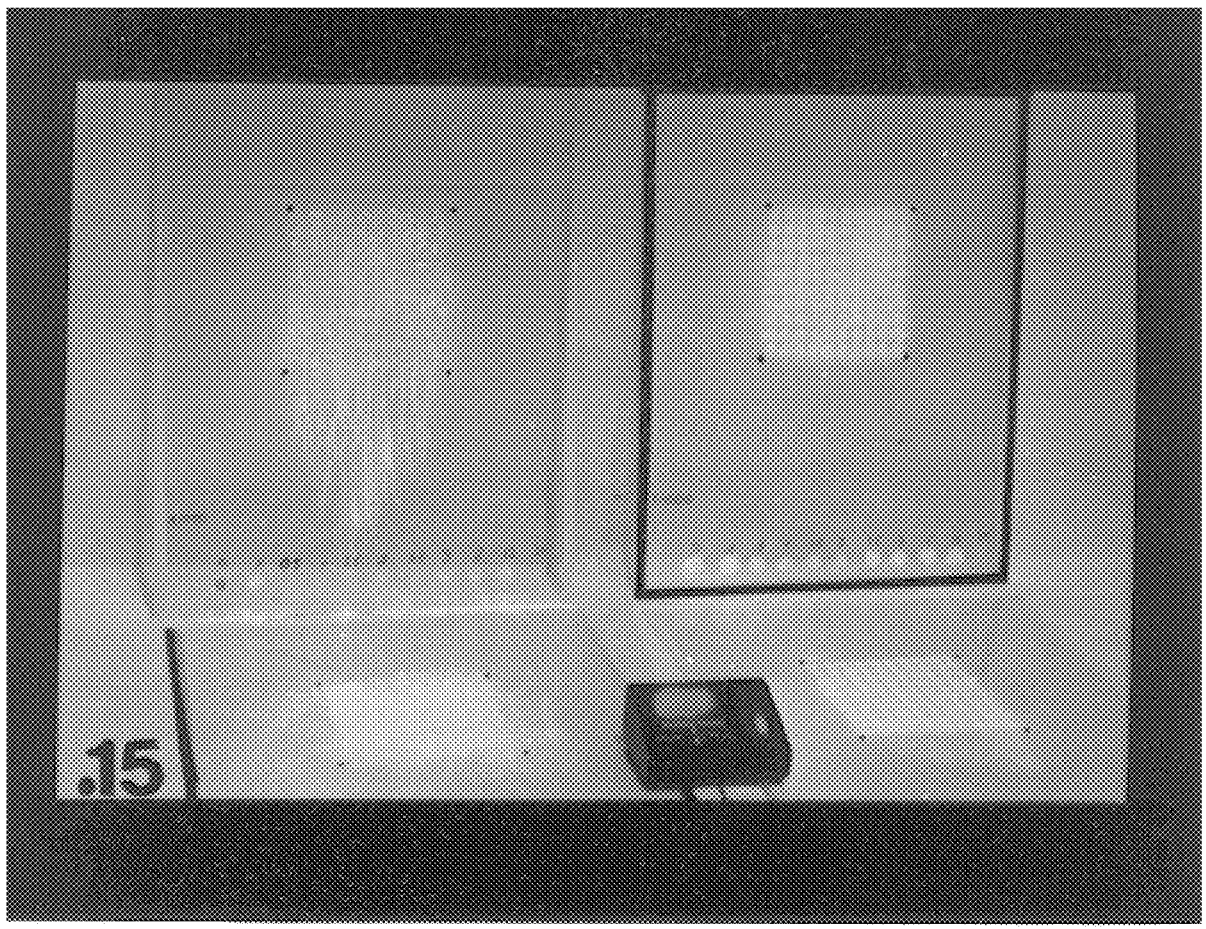
FIG. 2 is a photograph taken under alternate light, showing the two vertically-positioned and two horizontally-positioned glass panes of FIG. 1, after application of the fluorescin reagent without thickener (left panes) and with thickener (right panes) according to the method described herein; the left panes show diffusion (on the horizontal pane) and running of the signal (on the vertical pane), and the right panes show clearly the punctate pattern of the blood samples.

FIGS. 1 and 2 demonstrate the problematic nature of fluid double reagent systems (fluorescin and $H_2O_2$), on a non-porous substrate (glass panes). The two glass panes on the right in FIG. 2 illustrate the improvement with the thickener additive (KELTROL RD™) compared to using the unthickened fluorescein reagent on the two panes on the left. Although both unthickened and thickened fluorescin reagent solutions were capable of producing detectable fluorescence, the unthickened fluid showed substantial running, especially on the vertical pane, and smearing of the bloodstain pattern. In contrast, the pattern was clearly visible on both the vertical pane and the horizontal pane tested with the thickened fluorescin reagent solution. In fact, as shown in FIG. 2, the sensitivity was slightly greater with the thickener added, probably due to stabilizing the reagents on the bloodstain, allowing the reagents more time to react before any distortion of the pattern occurred due to diffusion.

EXAMPLE 5
Detection of Blood Patterns in Latent Bloodstains on Flooring Materials Previous fluorescent detection techniques for this technique have not been effective in distinguishing class characteristics of shoe prints on various substrates, including carpeting. The present method has sufficient sensitivity to detect details of footprints made with small amounts of blood adhered to the bottom of shoes.

In this test, a series of bloodstained footprints were prepared on standard flooring materials such as linoleum tiles and carpeting (both shag and berber types) by having a person wearing rubber soled sport shoes step in human blood and then walk or jump along the flooring material. With successive steps or applications of the shoe to the flooring, less blood from the sole of the show was deposited on the flooring material. Thus, initially bloodstained shoe prints were clearly visible and later no blood was visible to the naked eye under normal light. The entire area on which the shoe prints had been deposited was treated using the fluorescein detection method. That is, the area was first sprayed with a nebulized thickened 1:50 fluorescin reagent solution using a pressurized spray device. A low pressure (less than 30 psi), high volume (LPHV) spray gun was used because this device has sufficient power to spray a thickened fluorescein reagent solution and deliver the reagent in a confined and detailed manner, reducing the change of overspray. Because noxious NaOH fumes were emitted when the gun was powered, a particle face mask was used during spraying. The thickened fluorescin reagent solution was sprayed on the carpeting a second time and then a 3% hydrogen peroxide solution was sprayed on the area previously sprayed with the fluorescin reagent. The area was then illuminated with a 450 nm light source (while the user wore UV protective eyewear) and photographed using a camera with a standard photographic supplier's yellow barrier filter.

Figure 3:
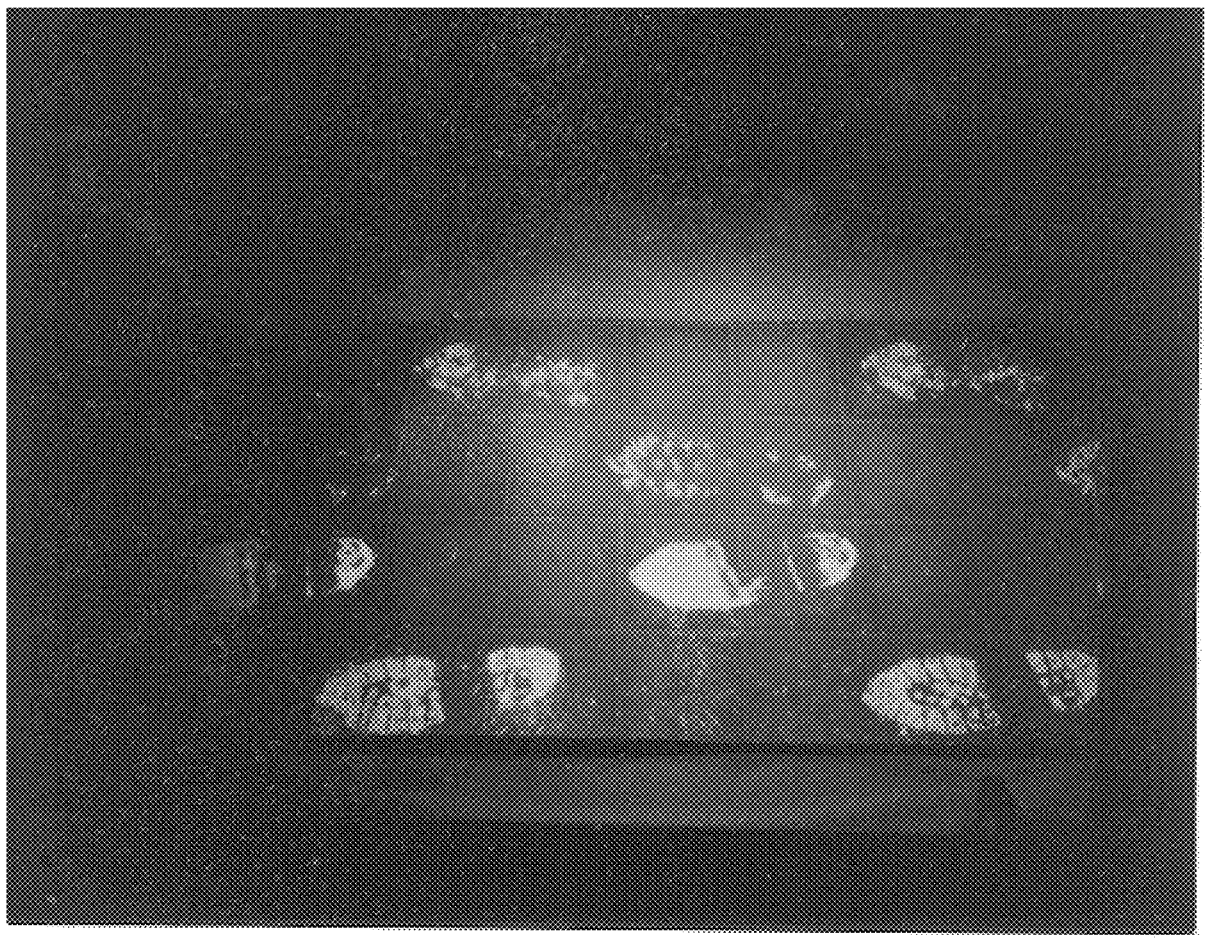
FIG. 3 is a photograph taken under alternate light of bloody shoe prints made on a solid flooring surface and treated according to the fluorescein method described herein.
Figure 4:
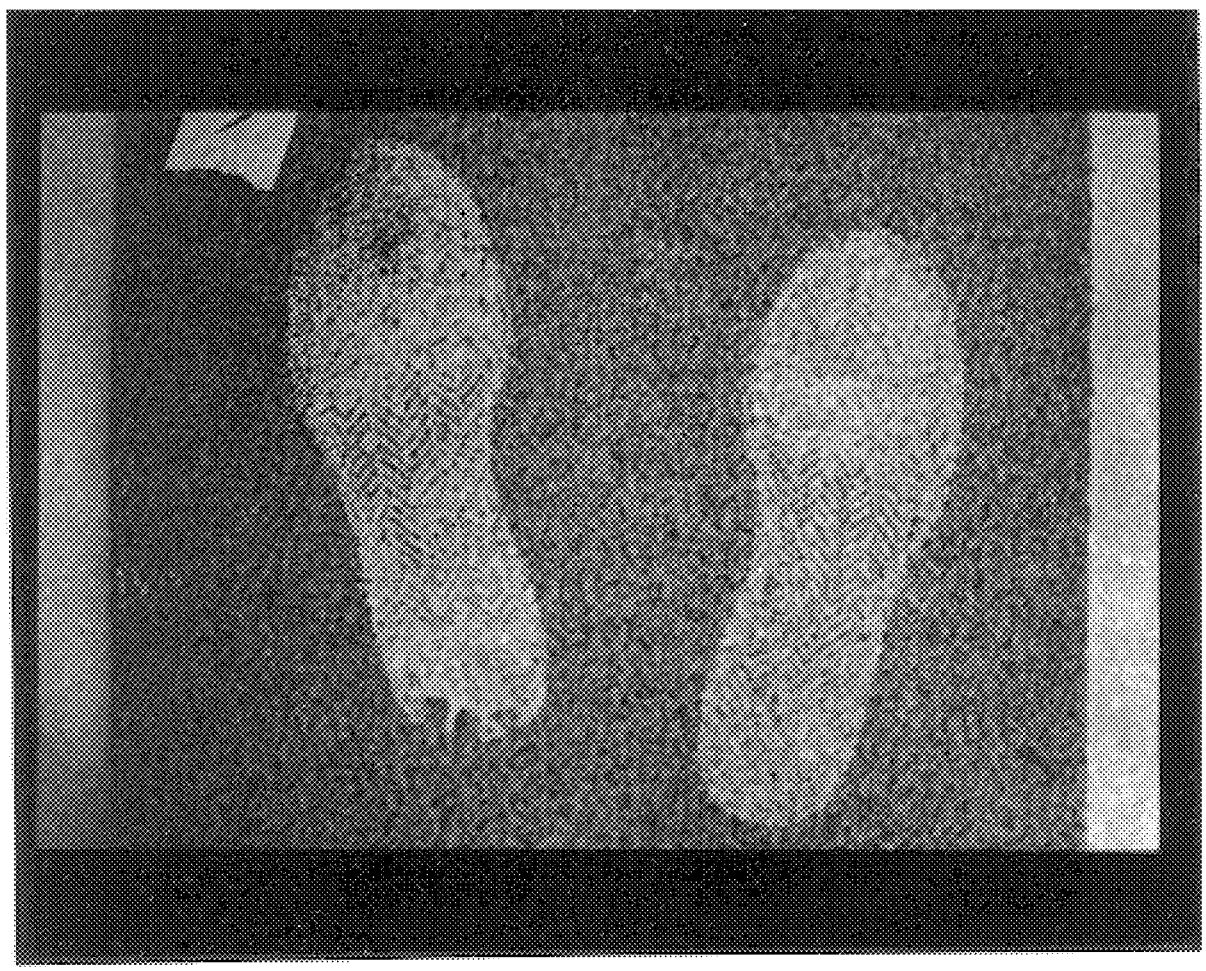
FIG. 4 is a photograph taken under alternate light of bloody shoe prints made on carpeting and treated according to the fluorescein method described herein.

FIG. 3A shows a series of prints made on linoleum tiles, and FIG. 3B shows a left and a right shoe print on carpeting. The different intensities of prints made by successive contacts to the flooring material (i.e., depositing less blood) is shown in FIG. 3A.

The results of this study showed that all shoe prints that were visible without fluorescin treatment (i.e., visible bloodstains) were readily detected with the fluorescein detection method. In fact, the amount of fluorescence detected was so great that the initial shoe prints appeared almost solid with no detail of the shoe bottom seen other than the shoe outline. For later shoe prints in the series, more detail of the sole pattern was readily detected. For example, the shoe prints shown in FIG. 3B show that the left shoe contained two worn spots on the heel (that did not deposit blood) which were not present on the right shoe. For latent bloodstains, where essentially no shoe print was visible without fluorescin treatment, the shoe prints were clearly detected and details of the sole pattern (i.e., the pattern of ridges and grooves, the manufacturer's name and unique wear patterns seen on the particular shoes used) were readily detected in the photographs of the fluorescent patterns detected after use of the fluorescein detection method. These results show that this method is effective for detecting latent bloodstains in a simulated field situation and provide additional evidentiary information such as the size, manufacturer and wear patterns of the shoes worn that created the latent stains, and the direction the wearer walked from the spot where blood first contacted the shoes.

EXAMPLE 6
Kit for Practicing the Method

A kit containing all the needed reagents to practice the method yields greater latitude to investigators who have geographically large jurisdictions, and where transporting reagent from the laboratory to the crime scene is not practical for time or distance reasons. Because the simplified procedure for producing the fluorescin reagent solution described in Example 1 requires less equipment and skill level to prepare the fluorescin reagent, personnel skilled in the art are capable of performing this task, thus providing more immediate results in the field.

A kit for practicing this fluorescein detection method includes the following components for making the reagents in the field: sodium hydroxide, preferably already made to a 10% solution and stored in a non-reactive plastic container, zinc particles, fluorescein, a thickening agent, preferably already made to the proper viscosity for making the diluted fluorescin reagent solution, and hydrogen peroxide, preferably provided at a dilution of 3% to 10% in a hand spray pump bottle. The kit may include sufficient deionized water to make the fluorescin reagent substantially as described in Example 1, or the user may supply this component. Preferably, all of the dried compounds (e.g., fluorescein, zinc particles and NaOH if not provided as a solution) are provided in measured aliquots sufficient for producing the fluorescin reagent. If deionized water is provide, it is preferably premeasured in a container suitable for preparing the 10% NaOH solution and then gently boiling the fluorescein solution with zinc. A clean container (e.g., a clean spray container having the capacity to be pressurized) may also be provided in the kit or provided by the user. Equipment for preparing reagents (e.g., glassware, heating and stirring devices, spraying devices) may be included in a kit, although such materials are generally reusable and are generally provided by the user. Similarly, documentation equipment (cameras and photographic supplies) may be provided in a kit but generally are provided by the user.

Using the methods described herein a user skilled in the art can readily produce the reagents and practice the fluorescein method in the field, such as at a crime scene.

Documentation Guidelines

For use in the field, the following guidelines should be used when practicing this method for documentation of the results. The fluorescence obtained from a bloodstain can be documented using still photography or a video camcorder. The scene should be photographed prior to the fluorescin application. The substrate with the suspected bloodstain may then examined for any inherent fluorescence and any results should be documented by photography.

Prior to application, the fluorescin reagent should be tested on sample blood and checked for the proper reaction. A blood pattern on a glass pane (similar to that shown in FIG. 2) may be brought to the scene and the reagents tested thereon before application of the reagents to the material suspected of containing blood. This control should be documented to show that the reagents are working at the time the test is performed. Preferably, the reagent is also applied on a like substrate (e.g., an area of the same materials but outside of the area where blood is suspected to be found), checked for cross-reactivity and the results documented. The reaction may be visualized and photographed with and without the use of an orange or yellow barrier filter, although the barrier filter generally provides greater resolution on the resulting photograph. Unlike luminol photography, the scene does not need to be completely darkened for the reaction to be visualized and photographed. Some ambient light in the scene will aid the photographer/investigator in later orienting the scene and its contents in the resulting documentation. This property alleviates the need for flash (or "fill") photography to document the scene independent of the photography used to document the results of the fluorescein method.

Photographic documentation of the fluorescin reaction is best accomplished with a tripod-stationed 35 mm camera with the aperture set of $f8$ using an orange or yellow barrier filter and color print film (e.g., Kodak EI400). The exposure times should be varied between about 5 sec and 30 sec, depending upon the lighting conditions at the scene. Photographs may also be taken utilizing the aperture-priority automatic function of the camera, resulting in better quality photographs.

The fluorescin reaction can occur for several minutes before the bloodstain pattern begins to degrade (e.g., smear) and background fluorescence becomes problematic This allows ample time for photographers to vary their exposures and document the scene with and without the barrier filters.

The fluorescein detection method described herein has been used successfully to detect bloodstains on a variety of surfaces and articles associated with a number of crime scenes including residences (flooring, stairs, carpeting, interior walls), motor vehicles (interior seats and carpeting, exterior surfaces of a car, tailgate and cargo area of a pickup truck, interior of a trailer unit), articles of clothing (washed jacket and shoes) and metal tools (washed pocket knife, tire iron and lug wrench).

While particular embodiments of the invention have been described in detail, it will be apparent to those skilled in the art that these embodiments are exemplary rather than limiting, and the true scope of the invention is defined by the claims that follow.

I claim:

1. A method for detecting latent blood on a solid surface, comprising the steps of:

providing a surface suspected of containing a latent bloodstain;

spraying said surface with a fluorescin reagent solution comprising about 0.006% to about 0.33% fluorescing 0.06% to about 3.33% sodium hydroxide and an alkaline-insensitive thickening agent in an aqueous solution;

then spraying said surface with an about 2% to about 15% hydrogen peroxide solution; and detecting fluorescence emitted from fluorescein that results from conversion of fluorescin to fluorescein due to the presence of latent blood contained on the surface.

2. The method of claim 1, wherein the spraying step with a fluorescin reagent solution is repeated before the spraying step with a hydrogen peroxide solution.

3. The method of claim 1, wherein the spraying step with a fluorescin reagent solution is performed using a pressurized spray device.

4. The method of claim 1, wherein the spraying step with a hydrogen peroxide solution is performed using a hand pump spray device.

5. The method of claim 1, wherein the detecting step includes illuminating the surface with an alternate light source of about 435 nm to about 505 nm.

6. The method of claim 1, wherein the detecting step includes illuminating the surface with a 450 nm light source and photographically documenting the fluorescence emitted.

7. The method of claim 1, wherein the fluorescin reagent solution is prepared from about a 1:3 to about 1:150 dilution of a first solution of about 1% fluorescin and 10% sodium hydroxide, in a second aqueous solution containing an alkaline-insensitive water soluble gum.

8. The method of claim 7, wherein the second aqueous solution contains about 1% to about 10% of an alkaline-insensitive water soluble gum.

9. The method of claim 7, wherein the second aqueous solution contains about 0.5% Xanthan gum.

10. The method of claim 1, wherein the hydrogen peroxide solution is about 3% to about 10% hydrogen peroxide.

11. The method of claim 1, wherein the detecting step is capable of detecting blood diluted about 1:6,000 to about 1:105,000.

12. The method of claim 1, wherein the detecting step is capable of detecting blood diluted about 1:6,000 to about 1:75,000.

13. The method of claim 1, wherein the detecting step is capable of detecting blood diluted about 1:6,000 to about 1:15,000.

14. The method of claim 1, wherein the detecting step is capable of detecting latent blood on a nonporous, vertical or uneven surface and retaining a pattern of the latent blood for sufficient time to allow documentation of the fluorescence emitted.

* * * * *